United States Patent
Bhushan (10) Patent No.: US 11,419,883 B2
(45) Date of Patent: Aug. 23, 2022

(54) INHIBITING SENESCENT PROCESSES IN BETA CELLS FOR THE PREVENTION OF TYPE 1 DIABETES

(71) Applicant: The Regents of the University of California, Oakland, CA (US)

(72) Inventor: Anil Bhushan, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/611,158

(22) PCT Filed: May 4, 2018

(86) PCT No.: PCT/US2018/031161
§ 371 (c)(1),
(2) Date: Nov. 5, 2019

(87) PCT Pub. No.: WO2018/204830
PCT Pub. Date: Nov. 8, 2018

(65) Prior Publication Data
US 2020/0078376 A1    Mar. 12, 2020

Related U.S. Application Data (60) Provisional application No. 62/501,805, filed on May 5, 2017.

(51) Int. Cl.
| | | |
|---|---|---|
| *A61K 31/635* | (2006.01) | |
| *A61P 3/10* | (2006.01) | |
| *A61K 31/12* | (2006.01) | |
| *A61K 31/145* | (2006.01) | |
| *A61K 31/353* | (2006.01) | |
| *A61K 31/4025* | (2006.01) | |
| *A61K 31/41* | (2006.01) | |
| *A61K 31/427* | (2006.01) | |
| *A61K 31/437* | (2006.01) | |
| *A61K 31/4412* | (2006.01) | |
| *A61K 31/45* | (2006.01) | |
| *A61K 31/4545* | (2006.01) | |
| *A61K 31/4725* | (2006.01) | |
| *A61K 31/496* | (2006.01) | |
| *A61K 31/506* | (2006.01) | |
| *A61K 31/517* | (2006.01) | |
| *A61K 31/519* | (2006.01) | |
| *A61K 31/5377* | (2006.01) | |
| *A61K 31/541* | (2006.01) | |
| *A61K 31/5415* | (2006.01) | |
| *A61K 31/55* | (2006.01) | |
| *A61K 31/551* | (2006.01) | |
| *A61K 31/5517* | (2006.01) | |

(52) U.S. Cl.
CPC ............ *A61K 31/635* (2013.01); *A61K 31/12* (2013.01); *A61K 31/145* (2013.01); *A61K 31/353* (2013.01); *A61K 31/4025* (2013.01); *A61K 31/41* (2013.01); *A61K 31/427* (2013.01); *A61K 31/437* (2013.01); *A61K 31/4412* (2013.01); *A61K 31/45* (2013.01); *A61K 31/4545* (2013.01); *A61K 31/4725* (2013.01); *A61K 31/496* (2013.01); *A61K 31/506* (2013.01); *A61K 31/517* (2013.01); *A61K 31/519* (2013.01); *A61K 31/5377* (2013.01); *A61K 31/541* (2013.01); *A61K 31/5415* (2013.01); *A61K 31/55* (2013.01); *A61K 31/551* (2013.01); *A61K 31/5517* (2013.01); *A61P 3/10* (2018.01)

(58) Field of Classification Search
CPC ................................ A61P 3/10; A61K 31/635
See application file for complete search history.

(56) References Cited

U.S. PATENT DOCUMENTS

2016/0297826 A1    10/2016  Masse et al.
2017/0216286 A1    8/2017   Kirkland et al.

FOREIGN PATENT DOCUMENTS

| KR | 10-1750994 B1 | 6/2017 |
| WO | 2016127135 A1 | 8/2016 |
| WO | 2017008060 A1 | 1/2017 |

OTHER PUBLICATIONS

Zhu et al. Aging, 2017, vol. 9, 9 pages (Year: 2017).*
Mayo Clinic, "Type 1 diabetes—Symptoms and Causes" (https://www.mayoclinic.org/diseases-conditions/type-1-diabetes/symptoms-causes/syc-20353011?p=1; 4 pages) (Accessed Oct. 14, 2021) (Year: 2021).*
Mayo Clinic, "Type 1 diabetes—Diagnosis and Treatment" (https://www.mayoclinic.org/diseases-conditions/type-1-diabetes/diagnosis-treatment/drc-20353017?p=1; 12 pages) (Accessed Oct. 14, 2021) (Year: 2021).*
Konopleva et al. Cancer Discovery, Oct. 2016, pp. 1106-1117 (Year: 2016).*
Maciel et al. Biomedicine & Pharmacotherapy, 2016, vol. 84, pp. 559-568 (Year: 2016).*
Tough, David F. et al., "Immune disease-associated variants in gene enhancers point to BET epigenetic mechanisms for therapeutic interventenhancers point to BET epigenetic mechanisms for therapeutic intervention", Epigenomics, 2016, vol. 8, No. 4, pp. 573-584. See pp. 578-579.

(Continued)

*Primary Examiner* — James D. Anderson (57) ABSTRACT

The inventor of the present disclosure has advantageously elucidated the role of senescent processes in the development of Type 1 diabetes. Genotoxic stress responses, senescence, and acquisition of a SASP condition in beta cells are drivers that progress at-risk individuals to overt Type 1 diabetes. The administration of senolytic agents to at risk individuals selectively removes senescent cells and relieves beta cells from the factors which drive the development of overt Type 1 diabetes. Accordingly, Type 1 diabetes can be prevented in at-risk individuals by the administration of senolytic compositions. Additionally, given the major role of SASP in the development of Type 1 diabetes, the inhibition of SASP factors may be used to prevent Type 1 diabetes.

2 Claims, 1 Drawing Sheet

(56) References Cited

OTHER PUBLICATIONS

Mollah, Zia U. A. et al., "Abnormal NF-KB function characterizes human type 1 diabetes dendritic ce 11 s and monocyt es", The Journal of Immunology, 2008, vol. 180, No. 5, pp. 3166-3175. See abstract; and pp. 3166, 3167, 3171.

Cao, Zhao-Hui et al., "Caspase-3 is involved in IFN-y- and TNF-a-mediated MIN6 cells apoptosis via NF-KB/Bcl-2 pathway", Cell Biochemistry and Biophysics, 2013, vol. 67, Issue 3, pp. 1239-1248. See pp. 1240, 1243, 1246.

Pihoker et al., 2005. Autoantibodies in diabetes. Diabetes 54: S52-S61.

Miao et al., 2007. Role of Autoantibodies in Type 1 Diabetes, Frontiers in Bioscience 12: 1889-1898.

Chaparro and DiLorenzo, 2010, An update on the use of NOD mice to study autoimmune (Type 1) diabetes, Expert Rev. Clin. Immunol. 6:939-955.

Thayer et al., 2010. Use of NOD Mice to Understand Human Type 1 Diabetes, Endocrinol Metab Clin North Am 39:541-561.

\* cited by examiner

INHIBITING SENESCENT PROCESSES IN BETA CELLS FOR THE PREVENTION OF TYPE 1 DIABETES

CROSS-REFERENCE TO RELATED APPLICATIONS

This application is a § 371 national stage filing of International Application No. PCT/US2018/031161, entitled "Inhibiting Senescent Processes in Beta Cells for the Prevention of Type 1 Diabetes," filed on May 4, 2018, which claims priority to U.S. Provisional Application No. 62/501,805, entitled "Inhibiting Senescent Processes in Beta Cells for the Prevention of Type 1 Diabetes," filed on May 5, 2017, each of which is incorporated by reference herein in its entirety.

STATEMENT REGARDING FEDERALLY SPONSORED RESEARCH OR DEVELOPMENT

Not Applicable.

BACKGROUND OF THE INVENTION

Replicative senescence is a pathway that protects against unrestricted cell proliferation. Aging cells accumulate DNA-damaging insults which create the risk of genetic instability and cancer. In response to such DNA damage, some cells undergo apoptosis. Others enter a state called cellular senescence, wherein the cell cycle is arrested to inhibit the proliferation of damaged cells. Individuals generally accumulate such senescent cells with age.

In some cases, an extended state of unresolved stress causes the senescent cells to exhibit what is known as the SASP, for senescence-associated secretory phenotype. SASP cells secrete a number of inflammatory signal molecules, including cytokines, chemokines, and other factors. This SASP secretome may profoundly affect neighboring, non-senescent cells, impairing their function and facilitating their transition to senescent cells as well.

Accordingly, the use of senolytic agents, agents which selectively kill senescent cells, has been proposed for the treatment of various age-related diseases. Further, the use of senolytics to treat diabetes has been proposed, for example in United States Patent Application Publication Number US20170216286, "Killing senescent cells and treating senescence-associated conditions using a src inhibitor and a flavonoid," by Kirkland et al. Likewise, the administration of senolytic agents to treat diabetes is contemplated in PCT International Patent Application Number WO2017008060, "Compositions and methods for treating senescence-associated diseases and disorders," by Lopez-Dominguez.

Senolytic agents have been proposed for the treatment of Type II diabetes [for example, as described in Palmer et al., 2015, "Cellular Senescence in Type 2 Diabetes: A Therapeutic Opportunity," Diabetes 64(7): 2289-2298]. In Type II diabetes, senescence is triggered in pancreatic islet β cells by unknown mechanisms, arresting the cell cycle. Cumulatively, this loss of self-replicating capability in β cells leads to a decrease in β cell numbers and islet mass, reducing the production of insulin, which in turn results in dysregulated glucose metabolism, hyperglycemia and diabetes [for example, as described in Tavana and Zhu, 2011, "Too many breaks (brakes): Pancreatic β-cell senescence leads to diabetes," Cell Cycle, 10:15, 2471-2484.

In contrast, Type I Diabetes comprises a different pathology. In Type 1 diabetes, pancreatic β cells are attacked by autoimmune processes, with invasion of the islets by inflammatory cells in a condition called insulitis. Over time, this sustained autoimmune process results in the loss of large numbers of β cells and dysregulation of glucose metabolism [for example, as described in Cnop et al., 2005, "Mechanisms of Pancreatic-Cell Death in Type 1 and Type 2 Diabetes-Many Differences, Few Similarities," Diabetes 54 (supplement 2) S97-S107]. It is known that beta cells undergo age-related senescence, however the role of stress-induced senescence and acquisition of SASP fate in beta cells has not been explored. Accordingly, there is a need in the art for an understanding of the role of senescent processes in Type I diabetes, and there remains a continued need for interventions to prevent and treat this condition.

SUMMARY OF THE INVENTION

Provided herein are novel insights into the development and progression of Type 1 diabetes and the role of senescent processes therein. The inventors of the present disclosure have made the novel discovery that senescence is an integral process in the progression of Type 1 diabetes and that the SASP phenotype is a contributing pathological factor. The inventors of the present disclosure have further demonstrated that senolytic agents may be administered during critical early phases of Type 1 diabetes development and can be used to prevent the onset or reduce the severity of the disease.

The inventors of the present disclosure have determined that genotoxic stresses present in the development of Type 1 diabetes create a stress-induced senescent phenotype. The inventors of the present disclosure have also determined that this stress response, if sustained and unresolved, leads to the manifestation of the SASP condition in beta cells and that this has pathological effects on surrounding, non-senescent cells and islet function. The inventors of the present disclosure have further demonstrated that administration of senolytic agents can disrupt the transition from stress-response senescent phenotype to SASP phenotype, preventing the onset or reducing the severity of Type 1 diabetes. The inventors of the present disclosure have further demonstrated that the selective removal of senescent beta cells comprises an effective treatment for Type 1 diabetes. Furthermore, the inventors of the present disclosure have determined that immune infiltration of islet cells can be ameliorated by the administration of senolytic agents.

Accordingly, in one aspect, the scope of the invention encompasses methods of preventing Type 1 diabetes by administration of a senolytic agent to a subject at risk of Type 1 diabetes. Various novel criteria for identifying subjects as at-risk are disclosed herein.

In another aspect, the scope of the invention encompasses a method of treating Type 1 diabetes in a subject by the administration of a senolytic agents. In another aspect, the scope of the invention encompasses the administration of a senolytic agent to disrupt immune infiltration of islet beta cells.

The various embodiments of the invention are described next.

DETAILED DESCRIPTION OF THE INVENTION

Inhibition of Senescent Processes. The scope of the invention encompasses methods for inhibiting various pathological senescent processes in beta cells.

In a first aspect, the scope of the invention encompasses a method of preventing Type 1 diabetes in a subject at risk therefore by the administration to the subject of a senolytic agent. In a related implementation, the invention comprises a senolytic agent for use in the prevention of Type 1 diabetes. In a related implementation, the scope of the invention encompasses the use of a senolytic agent in the manufacture of a medicament for the prevention of Type 1 diabetes.

As used herein, Type 1 diabetes refers to Diabetes mellitus, Type 1, as known in the art. This form of diabetes is caused by autoimmune destruction or impairment of beta cells, manifesting in reduced insulin production, and dysregulated glucose metabolism. As used herein, beta cell refers to pancreatic islet beta cells, as known in the art. For example, beta cells may be identified by their non-immune status (e.g CD45 negative) and markers of beta cell identity such as Ins1 and Ins2. As used herein, the "beta cell environment" or "islet environment" refers to pancreatic regions harboring beta cells, including islets, and the surrounding tissues and interstitial fluids to which beta cells are exposed.

As used herein, "prevention of diabetes" means any inhibition of the progression from non-overt diabetic status to overt Type 1 diabetic status. Prevention may encompass the slowing, arrest, delay, amelioration of symptoms, or other inhibition of diabetic progression from a non-overt diabetic status to diabetic status. Overt diabetes is characterized by elevated fasting blood glucose concentration (e.g. greater than 130 mg/dl when fasting) and other classical symptoms such as insufficient insulin production, hyperglycemia, diabetic ketoacidosis, and other symptoms of Type 1 diabetes.

In a second aspect, the invention encompasses a method of reducing the number of senescent beta cells in a subject at risk for Type 1 diabetes, by the administration of a senolytic agent. As demonstrated herein, the genotoxic stress associated with the onset of Type 1 is present in beta cells prior to the onset of diabetes and precedes the acquisition of SASP. Senolytic agents destroy cells that are undergoing the transition to the senescent state and cells which have attained a senescent state, preventing their paracrine pro-senescent effects on neighboring, non-senescent cells. The method may achieve a reduction in the absolute number of senescent beta cells or a reduction in the proportion of senescent beta cells to non-senescent beta cells. In one embodiment, the treatment comprises reducing the proportion of senescent beta cells to less than 25% of total beta cells, less than 20% of total beta cells, less than 15% of total beta cells, less than 10% of total beta cells, or less than 5% of total beta cells.

In a related implementation, the invention comprises a senolytic agent for use in reducing the abundance of senescent beta cells in a subject at risk of Type 1 diabetes. In a related implementation, the scope of the invention encompasses the use of a senolytic agent in the manufacture of a medicament for reducing abundance of senescent beta cells in a subject at risk of Type 1 diabetes.

In a third aspect, the scope of the invention encompasses reducing the abundance of SASP beta cells in a subject, for example, a subject at risk for Type 1 diabetes, by administration of a senolytic agent. As demonstrated herein, a SASP inflammatory condition is acquired by a substantial number of beta cells in the progression of Type 1 diabetes and such phenotype has deleterious effects on surrounding, non-senescent beta cells. Accordingly, the scope of the invention encompasses methods of reducing the abundance of beta cells having SASP phenotype, by removal of senescent cells with the SASP phenotype. The method may achieve a reduction in the absolute number of SASP beta cells or a reduction in the proportion of SASP cells to non-senescent beta cells. In one embodiment, the treatment comprises reducing the proportion of SASP beta cells to less than 25% of total beta cells, less than 20% of total beta cells, less than 15% of total beta cells, less than 10% of total beta cells, less than 5% of total beta cells, or less than 1% of total beta cells.

SASP beta cells will be defined as those expression or exhibiting any known biomarkers of the SASP condition, including the secretion of pro-inflammatory signaling molecules. Exemplary SASP biomarkers include drivers of SASP such as bromodomain and extra-terminal motif (BET) proteins (e.g. BRD2, BRd3, and BRD4), p38MAPK, JAK, NF-κB, and CCAAT-enhancer-binding proteins (C/EBP). SASP incidence may also be assessed by the presence of secreted SASP factors in the islet cell environment, for example, secreted factors such as IL-6, Serpine1, G-CSF, Cc12, Mmp9, Mmp12, Igfpb3, IL1, IL8, CXCL1, CXCL2, monocyte chemotactic protein 3, insulin-like growth factor-binding proteins (including IGFBP2, IGFBP3, IGFBP4, IGFBP5, and PGFBP6), colony stimulating factor, MMP-3, MMP-10, and serine proteases.

Bcl-2 and other antiapoptotic proteins are upregulated in the SASP condition. Accordingly, senolytic compounds that target Bcl-2 family members will, generally, remove SASP beta cells while sparing non-SASP senescent cells. In one implementation, the methods of the invention encompass the administration of a senolytic agent that preferentially or selectively kills SASP beta cells, for example, inhibitors of BCl-2 family members.

In a related implementation, the invention comprises a senolytic agent for use in reducing the abundance of SASP beta cells of a subject, for example, a subject at risk for Type 1 diabetes. In a related implementation, the scope of the invention encompasses the use of a senolytic agent in the manufacture of a medicament for reducing the abundance of SASP beta cells of a subject, for example, a subject at risk for Type 1 diabetes.

In a fourth aspect, the scope of the invention encompasses a method of reducing the abundance of one or more pro-senescent and/or inflammatory factors in the islet cell environment of a subject, for example, a subject at risk for Type 1 diabetes, by the administration of a senolytic agent. As demonstrated herein, beta cells in the vicinity of senescent cells having a SASP condition are exposed to inflammatory and/or pro-senescent factors secreted by such SASP beta cells, with deleterious effects. The method of the invention encompasses the reduction of such factors in the environment of healthy beta cells by selectively removing senescent cells. The one or more SASP factors may be selected from the group consisting of secreted factors such as Serpine1, G-CSF, Cc12, Igfpb3, IL6, IL1, IL8, Fnlb, CXCL1, CXCL2, monocyte chemotactic protein 3, insulin-like growth factor-binding proteins (including IGFBP2, IGFBP3, IGFBP4, IGFBP5, and PGFBP6), colony stimulating factor, MMP-2, MMP-3, MMP-9, MMP-10, MMP-12 and serine proteases.

In a related implementation, the invention comprises a senolytic agent for use in reducing the abundance of one or more pro-senescent and/or inflammatory factors in the islet cell environment of a subject, for example, a subject at risk for Type 1 diabetes. In a related implementation, the scope of the invention encompasses the use of a senolytic agent in the manufacture of a medicament for reducing the abundance of one or more pro-senescent and/or inflammatory factors in the islet cell environment of a subject, for example, a subject at risk for Type 1 diabetes.

In a fifth aspect, the scope of the invention encompasses a method of inhibiting immune infiltration of islet cells of a subject, for example, a subject at risk of Type 1 diabetes, by the administration of a senolytic agent. Immune infiltration is a major driver of insulitis and the progression to Type 1 diabetes and is promoted by senescent and SASP cells. For example, as demonstrated herein, administration of senolytic agents inhibits chemotactic signaling by senescent cells that attracts monocytes to islets. Accordingly, in one embodiment, the invention comprises the administration of a senolytic agent to reduce the abundance of one or more immune cell types in the beta cell environment. In one embodiment, the one or more immune cell types comprises T lymphocytes, B lymphocytes, dendritic cells, or macrophages, including monocytes.

In a related implementation, the invention comprises a senolytic agent for use in inhibiting immune infiltration of islet cells of a subject, for example, a subject at risk of Type 1 diabetes. In a related implementation, the scope of the invention encompasses the use of a senolytic agent in the manufacture of a medicament for inhibiting immune infiltration of islet cells of a subject, for example, a subject at risk of Type 1 diabetes Senolytic Agents. The methods of the invention encompass the administration of a senolytic agent. The senolytic agent may comprise any composition of matter that facilitates or causes the selective death of cells that have acquired a senescent phenotype. As used herein, reference to "a senolytic agent" encompasses the administration of a pharmaceutically effective amount of one or more senolytic agents. Such pharmaceutically effective dosage can be determined by one of skill in the art. For example, dosages of 5-500 mg/kg, for example, 100 mg/kg, administered 1-7 days per week, for example 3 days per week. Where reference is made to the administration of compositions, it is understood that compositions may be formulated with any number of excipients, carriers, delivery vehicles, etc., as known in the art. It will be understood that the methods described herein encompass various delivery methods, including systemic delivery as well as localized delivery to the pancreas, including oral administration, intravenous administration, intraperitoneal injection, or by implanted devices.

In one implementation, the senolytic agent will comprise an agent which preferentially or selectively kills SASP beta cells. For example, the agent may comprise an inhibitor of one or more BCL-2 anti-apoptotic protein family members, for example an inhibitor of Bcl-2, Bcl-xL, Bcl-w or Mcl-1, which compositions preferentially trigger apoptosis in SASP beta cells. In one embodiment the senolytic agent is a BH3 mimetic, which can trigger apoptosis with some specificity in cells that have high levels of Bcl-2 or the related family members. In one embodiment, the senolytic agent is ABT-737, which targets Bcl-2 and family members Bcl-xL and Bcl-w. In one embodiment, the senolytic agent is ABT-199, which selectively targets Bcl-2. In one embodiment, the senolytic agent is Maritoclax, which targets Mcl-1. Another the senolytic agent which targets Bcl-2 family proteins is navitoclax (ABT263).

Other senolytic agents include: dasatinib; piperlongumin; MDM2 inhibitors; Akt inhibitors; WEHI-539; A1155463; A1331852, fisetin; Nutlin-3a; RG-1172, quercetin, enzastaurin, droxinostat, and EF-24 (1-(3,5-di-tert-butyl-4-hydroxyphenyl)-2-(3-ethyl-2-imino-2,3-dihydro-1H-benzimidazol-1-yl)ethanone hydrochloride).

In one implementation, the senolytic agent is an antibody, aptamer, targeted ubiquination construct, or other biological molecule, for example, comprising a peptide or nucleic acid, which selectively binds to antigens present on senescent and wherein such binding mediates, directly or indirectly, the death or elimination of such senescent cell or effector of senescence, for example by antibody dependent cell mediated cytotoxicity or similar processes.

Subjects at Risk of Type 1 Diabetes. The methods above may be applied to any animal subject, for example, human subjects or non-human animal subjects such as test animals or veterinary patients. In some implementations, the subject may be a subject that is at risk for Type 1 diabetes. As disclosed herein, subjects that progress to Type 1 diabetes undergo various senescence-related processes in beta cells that drive progression of the disease, prior to the onset of overt Type 1 diabetes. Accordingly, such subjects are amenable to the several methods of the invention which disrupt these senescent processes and the resulting progression to overt Type 1 diabetes.

In a first aspect, the subject at risk for Type 1 diabetes is a subject considered at risk of Type 1 diabetes according to known or classical classifications. In one embodiment, the subject is deemed at-risk by the presence of one or more Type 1 diabetes risk factors, including, for example, elevated blood glucose, family history, genetic biomarkers of Type 1 diabetes risk, excessive thirst, frequent urination, or other known indicators of Type 1 diabetes risk.

In one embodiment, the subject at risk for Type 1 diabetes is a subject that has been diagnosed as prediabetic, for example as having impaired fasting glucose or impaired glucose tolerance.

In one embodiment, the subject at risk for Type 1 diabetes is a subject that has been diagnosed as having "chemical diabetes" or the latent stage of Type 1 diabetes, for example, as characterized by abnormal glucose tolerance.

In one embodiment, the subject at risk for Type 1 diabetes is a subject that has been diagnosed with subclinical diabetes, for example, as characterized by abnormal glucose metabolism under stress.

In one embodiment, the subject at risk for Type 1 diabetes is a subject found positive for one or more diabetes autoantibodies. Exemplary autoantibodies include islet cell autoantibodies (ICA), antibodies to insulin (IAA), glutamic acid decarboxylase (GAA or GAD) and protein tyrosine phosphatase (IA2 or ICA512).

The inventor of the present disclosure, by elucidating the role of senescent processes in the progression to Type 1 diabetes, has advantageously identified novel criteria for identifying subjects that are at risk of developing Type 1 diabetes.

In one embodiment, the subject at risk of Type 1 diabetes comprises a subject that has incidence of genotoxic stress in beta cells. For example, the genotoxic stress may be assessed by the presence of one or more biomarkers selected from the group consisting of bromodomain and extra-terminal motif (BET) proteins (e.g. BRD2, BRd3, and BRD4), p38MAPK, JAK, NF-κB, and CCAAT-enhancer-binding proteins (C/EBP), DNA damage repair proteins 53BP1, NBS1, MDC1; DNA damage kinases ATM and ATR; and CHK1 and CHK2 kinases.

In one embodiment, the subject at risk of Type 1 diabetes comprises a subject that has an elevated abundance of senescent beta cells. For example, senescent beta cells may be identified by biomarkers of senescence such as nuclear p21; nuclear p16; BET proteins such as BRD2, BRD3, and BRD4; γ-H2AX (a phosphorylated form of the histone variant H2AX), CDCl25 phosphatases; p53, retinoblastoma tumor suppressor; senescence-associated β-galactosidase activity, senescence-associated heterochromatic foci in chromatin; and other markers of senescence known in the art. An elevated abundance of senescent cells may be assessed as any significant accumulation of senescent cells compared to appropriate controls (e.g. age matched healthy subject), for example, the significant abundance being up to 1% senescent cells to (as a fraction of total beta cells), up to 2% senescent cells, up to 5% senescent cells, up to 10% senescent cells, or great than 10% senescent cells.

In one embodiment, the subject at risk of Type 1 diabetes is a subject that has an inflammatory biomarker signature associated with the risk of Type 1 diabetes onset. In one embodiment, the inflammatory biomarker signature comprises one or more markers selected from the group consisting of Cxcl10, Igfbp4, Serping1 and down-regulation of mature beta cell markers Ucn3 and Iapp.

In one embodiment, the subject at risk of Type 1 diabetes comprises a subject that has incidence of SASP in beta cells. For example, SASP biomarkers include drivers of SASP such as bromodomain and extra-terminal motif (BET) proteins (e.g. BRD2, BRd3, and BRD4), p38MAPK, JAK, NF-κB, and CCAAT-enhancer-binding proteins (C/EBP). SASP incidence may also be assessed by the presence of secreted SASP factors in the islet cell environment, for example, secreted factors such as IL-6, Serpine1, G-CSF, Ccl2, Mmp9, Mmp12, Igfbp3, IL1, IL8, CXCL1, CXCL2, monocyte chemotactic protein 3, insulin-like growth factor-binding proteins (including IGFBP2, IGFBP3, IGFBP4, IGFBP5, and PGFBP6), colony stimulating factor, MMP-3, MMP-10, and serine proteases.

Advantageously, the inventor of the present disclosure has determined that the appearance of for one or more diabetes autoantibodies in a subject corresponds with the onset of SASP in beta cells. Accordingly, detection of one or more diabetes autoantibodies provides an indication that a subject will be amenable to the methods of the invention. Exemplary autoantibodies include islet cell autoantibodies (ICA), antibodies to insulin (IAA), glutamic acid decarboxylase (GAA or GAD) and protein tyrosine phosphatase (IA2 or ICA512). In one embodiment, the scope of the invention encompasses methods of reducing the abundance of SASP beta cells or reducing the abundance of SASP factors in a subject at risk of Type 1 diabetes, wherein the subject at risk of Type 1 diabetes comprises a non-diabetic subject having one or more detectable types of diabetes autoantibodies.

In one embodiment, the subject at risk of Type 1 diabetes comprises a subject that has enhanced chemotactic signaling for the attraction of one or more immune cell types, with greater chemotactic signaling than observed in healthy cells. Immune cell types may include T lymphocytes, B lymphocytes, dendritic cells, or macrophages, including monocytes.

Therapeutic Methods. Various embodiments of the invention are based on the inhibition of SASP factors. A SASP factor is any species that drives the SASP phenotype or which is secreted in the manifestation of the SASP phenotype. SASP factors include, for example, drivers of SASP such as bromodomain and extra-terminal motif (BET) proteins (e.g. BRD2, BRd3, and BRD4), p38MAPK, JAK, NF-κB, and CCAAT-enhancer-binding proteins (C/EBP). SASP factors further include, for example secreted factors such as IL-6, Serpine1, G-CSF, Ccl2, Mmp9, Mmp12, Igfpb3, IL1, IL8, CXCL1, CXCL2, monocyte chemotactic protein 3, insulin-like growth factor-binding proteins (including IGFBP2, IGFBP3, IGFBP4, IGFBP5, and PGFBP6), colony stimulating factor, MMP-3, MMP-10, and serine proteases In a first aspect, given the key role of SASP in driving the progression of Type 1 diabetes, the scope of the invention encompasses methods of inhibiting the deleterious effects of the SASP phenotype to prevent and treat Type 1 diabetes. Treatment of Type 1 diabetes, as used herein, encompasses any lessening or reversal of Type 1 diabetes symptoms or slowing or arresting the progression of the condition. Likewise, as SASP has been implicated in certain aspects of Type 2 diabetes, the scope of the invention encompasses the prevention or treatment of Type 2 diabetes, encompassing any lessening or reversal of Type 2 diabetes symptoms or slowing or arresting the progression of the condition, by the inhibition of a SASP factor.

In one embodiment, the method of the invention encompasses a method of preventing or treating Type 1 diabetes, in a subject at risk of or suffering therefrom, by the administration of an inhibitor of extra-terminal motif (BET) proteins (e.g. BRD2, BRd3, and BRD4), p38MAPK, JAK, NF-κB, and CCAAT-enhancer-binding proteins (C/EBP). In one embodiment, the BET inhibitor is selected from the group consisting of I-BET 762 (Glaxo Smith Kline), GSK525762 (Glaxo Smith Kline), OTX-015 (Merck), Ten-010 (Tensha pharmaceuticals), CPI-203 (Constellation Pharmaceuticals), CPI-0610 (Constellation Pharmaceuticals), RVX-208 (Resverlogix), LY294002, BMS-986158 (Bristol Myers Squibb), and PLX-51107. In one embodiment, the invention comprises a BET inhibitor for use in the prevention or treatment of Type 1 diabetes. In one embodiment, the invention comprises the use of a BET inhibitor in a method of making a medicament for the prevention or treatment of Type 1 diabetes. In one embodiment, the method of the invention encompasses a method of preventing or treating Type 2 diabetes, in a subject at risk of or suffering therefrom, by the administration of a BET inhibitor.

In one embodiment, the method of the invention encompasses a method of preventing or treating Type 1 diabetes, in a subject at risk of or suffering therefrom, by the administration of an inhibitor of bromodomain proteins. In one embodiment, the bromodomain inhibitor is BI-2536 or TG-101348. In one embodiment, the invention comprises a bromodomain inhibitor for use in the prevention or treatment of Type 1 diabetes. In one embodiment, the invention comprises the use of a bromodomain inhibitor in a method of making a medicament for the prevention or treatment of Type 1 diabetes. In one embodiment, the method of the invention encompasses a method of preventing or treating Type 2 diabetes, in a subject at risk of or suffering therefrom, by the administration of a bromodomain protein inhibitor.

In one embodiment, the method of the invention encompasses a method of preventing or treating Type 1 diabetes, in a subject at risk of or suffering therefrom, by the administration of an inhibitor of P38 MAPK. In one embodiment, the P38 MAPK inhibitor is selected from a group consisting of VX-745, VX-702, RO-4402257, SCIO-469, BIRB-796, SD-0006, PH-797804, AMG-548, LY2228820, SB-681323 and GW-856553. In one embodiment, the invention comprises a P38 MAPK inhibitor for use in the prevention or treatment of Type 1 diabetes. In one embodiment, the invention comprises the use of a P38 MAPK inhibitor in a method of making a medicament for the prevention or treatment of Type 1 diabetes. In one embodiment, the method of the invention encompasses a method of preventing or treating Type 2 diabetes, in a subject at risk of or suffering therefrom, by the administration of P38 MAPK inhibitor.

In one embodiment, the method of the invention encompasses a method of preventing or treating Type 1 diabetes, in a subject at risk of or suffering therefrom, by the administration of an inhibitor of JAK. In one embodiment, the JAK inhibitor is selected from the group consisting of roxolitnib, tofacitnib, olcacitnib, baricitnib, filgotinib, and lestauritnib. In one embodiment, the invention comprises a JAK inhibitor for use in the prevention or treatment of Type 1 diabetes. In one embodiment, the invention comprises the use of a JAK inhibitor in a method of making a medicament for the prevention or treatment of Type 1 diabetes. In one embodiment, the method of the invention encompasses a method of preventing or treating Type 2 diabetes, in a subject at risk of or suffering therefrom, by the administration of a JAK inhibitor.

In one embodiment, the method of the invention encompasses a method of preventing or treating Type 1 diabetes, in a subject at risk of or suffering therefrom, by the administration of an inhibitor of NF-κB signaling. In one embodiment, the NF-κB signaling inhibitor is selected from the group consisting of disulfram, olmesartan, and dithiocarbamates. In one embodiment, the invention comprises a NF-κB signaling inhibitor for use in the prevention or treatment of Type 1 diabetes. In one embodiment, the invention comprises the use of a NF-κB signaling inhibitor in a method of making a medicament for the prevention or treatment of Type 1 diabetes. In one embodiment, the method of the invention encompasses a method of preventing or treating Type 2 diabetes, in a subject at risk of or suffering therefrom, by the administration of an NF-κB inhibitor.

In another aspect, the scope of the invention encompasses methods of preserving beta cells in subjects having diabetes by the administration of a senolytic agent. Diabetic subjects, including subjects having Type 1 or Type 2 diabetes, have depleted numbers of healthy beta cells, which cells are lost by the ongoing underlying processes of these diabetic conditions. Removal of deleterious senescent cells will aid in the preservation of remaining healthy beta cells. Accordingly, the scope of the invention encompasses methods of preserving healthy beta cells in subjects having Type 1 or Type 2 diabetes by the administration of a senolytic agent. Preserving the number of healthy beta cells encompasses any treatment which prevents the death or incapacitation of beta cells in a treated subject, for example, in comparison to like untreated subjects. Likewise, the invention encompasses a senolytic agent for use in preserving healthy beta cells in subjects having Type 1 or Type 2 diabetes.

Diagnostic Methods. In one aspect, the scope of the invention encompasses methods of identifying subjects at risk of Type 1 diabetes. The risk of Type 1 diabetes may be based on the observation that the subject meets certain selected criteria. For example, the subject may be considered at risk of diabetes based on a criteria selected from the group consisting of: has been diagnosed as prediabetic; has been diagnosed as having subclinical diabetes; has been diagnosed as having chemical diabetes; has autoantibodies that target beta cells; has insulitis; has ongoing stress response processes in beta cells; has an inflammatory signature in beta cells; has a significant abundance of senescent beta cells; SASP condition is present in beta cells; has secreted SASP factors in the islet cell environment; has chemotactic signaling that promotes the infiltration of immune cells to the islet cell environment. Each such criteria may be established by the presence of one or more biomarkers, for example, as described in the preceding section.

In one aspect, the scope of the invention encompasses a method of ascertaining whether a subject is at risk of Type 1 diabetes, comprising the following process:
 a sample is obtained from the subject;
 the presence and/or abundance of one or more biomarkers associated with a selected at-risk criteria is assessed in the sample; and
 the subject is deemed to be at risk of Type 1 diabetes status if the sample is positive for the one or more biomarkers associated with the selected at-risk criteria.

The sample may comprise any sample appropriate for assessing the selected biomarkers. The sample may be any material withdrawn from the patient wherein the selected marker of beta cell senescent processes is measureable. For example, in some embodiments, the biomarker is present systemically and may be assessed in serum, urine, whole blood, saliva, etc. In some embodiments, the sample is a bone marrow derived sample, including any cells, fluids, or other materials present in bone marrow. In some embodiments, the sample is interstitial fluid from or from around the vicinity of the pancreas. The target biomarkers may be measured by any suitable means known in the art, for example by fluorescent antibody analysis, protein expression analysis, enzymatic assays, etc.

Engineered Cells. In one aspect, the scope of the invention encompasses engineered beta cells, wherein the engineered cells comprise one or more genetic modifications which inhibit the onset or manifestation of senescent processes, including the acquisition of the SASP phonotype. For example, the one or more genetic modifications may comprise the attenuation of senescence-associated genes, the attenuation of SASP-drivers, or the attenuation of secreted SASP factor genes. Attenuation may comprise, for example, gene silencing, mutation, or deletion.

The engineered cells of the invention may be used in the context of cellular therapy, for example in replacing or augmenting senescent beta cells with cells that are resistant to senescence or impaired in their ability to become senescent. The use of implanted beta cells for the treatment of Type I diabetes is known. For example, islet cells including beta cells and beta cell precursors have been implanted into patients, for example, to the pancreas. Implanted beta cells have also previously been implanted in the form of an artificial pancreas-type organ, for example, being implanted subcutaneously, or to the liver. In one implementation, the methods of the invention encompass the transplantation of senescence-resistant or senescence-impaired engineered beta cells or beta cell precursors to the body of the subject.

Examples. The following research summary describes various experiments which elucidate the role of senescent processes in beta cells in Type I diabetes and which demonstrate the efficacy of senolytic agents in disrupting senescence-related processes and preventing the onset of Type 1 diabetes.

Example 1. Beta cells acquire SASP during the progression of T1D in NOD mice. To identify changes in transcriptional signatures in the beta cells during the progression of the disease, differentially expressed RNA transcripts in islets from female euglycemic NOD mice were compared at 8 and 14 weeks by single-cell RNA sequencing. Beta cells (identified by high expression of Ins1 and Ins2) from 8 week and 14 week islets were clustered separately. Two transcriptomically-distinct clusters of beta cells were unique to 14-week beta cells. The relatively larger cluster expressed markers of cellular stress response primarily driven by the CDKI Cdkn1a (encoding p21) while the smaller one demonstrated a distinct inflammatory gene signature including Cxcl10, Igfbp4, and Serping1 and down-regulation of mature beta cell markers such as Ucn3 and Iapp. Expression of Cdkn1a and inflammatory markers Cxcl10, Serping1 and Igfbp4 were all increased on a global level in the beta cells of 14-week NOD mice compared with the 8-week mice. A two-dimensional (force-directed) nearest neighbor graph embedding, typically used to visualize continuous gene-expression topologies in high-dimensions, placed beta cells from these two 14-week-specific clusters along a common trajectory that progressed from cellular stress response to an inflammatory state.

Immunohistochemistry was used to assess expression of CDKIs, Cdkn2a (p16) and Cdkn1a (p21) and Ser139 phosphorylated Histone H2A.X (γ-H2A.X) as a measure of DNA damage. In C57BL6/J mice, the expression of p16 increased gradually during aging and accumulated in beta cells after 6 months of age, consistent with the onset of age-related senescence in beta cells. In contrast, Cdkn1a was not detected in islets at any age. However, in NOD mice Cdkn2a was already highly expressed in insulin-positive beta cells at 14-weeks of age. In addition, islets from 14-week old NOD mice showed increased expression of Cdkn1a and elevated levels of γ-H2A.X relative to 8-week mice. Thus the immunohistochemistry analysis is consistent with the scRNA-seq data in that during the progression of towards T1 D in NOD mice beta cells exhibit features of stress response senescence.

Hierarchical clustering analysis of the scRNA-seq data indicated that the cluster of beta cells that was segregated in the 14-week old NOD mice had an inflammatory signature related to SASP. Immunohistochemistry analysis showed that in contrast to 8 week old mice, insulin-expressing cells from 14-16 week old NOD mice co-stained for several SASP markers, including IL-6, Flnb and Mmp2. Moreover, SASP factors were not detected readily by immunostaining in the beta cells of aged (>20 month) C57BL/6 mice.

The secretome of islet cells from the 14-16 week NOD mice was analyzed. Islets depleted of CD45$^+$ cells were cultured in serum-free media and the resulting culture supernatant, hereafter referred to as conditioned media (CM) was analyzed using a bead-based multi-analyte luminex assay including a variety of key SASP factors and immune cell-specific non-SASP factors (IL-2, Granzyme B). Consistent with the immunohistochemistry analysis, the secretion of SASP factors (IL-6, Serpine1, G-CSF, Ccl2, Mmp9, Mmp12 and Igfpb3) was dramatically higher in the CD45-depleted islet cell populations from 14-week NOD mice as compared with 8-week mice. To determine the time-course of the stress response and SASP in beta cells, younger cohorts of 10 and 12-week old euglycemic NOD mice were analyzed by immunostaining for Cdkn1a and IL-6. At 10 weeks, Cdkn1a was detected in beta cells, but SASP marker IL-6 was not detected and at 12 weeks both senescence and SASP markers were evident in beta cells suggesting that the stress response precedes the acquisition of SASP. Taken together these data indicate that prior to hyperglycemia, beta cells harboring hallmarks of a senescence-like stress response accumulate in NOD mice that gradually acquire SASP by 12-16 weeks.

Example 2. Beta cell stress response senescence and SASP in human T1D. To determine whether beta cells undergo a stress response senescence and acquire SASP during the natural history of T1 D in humans, (SA-βgal) activity, a classical biomarker for senescent cells was assessed on pancreas sections from nondiabetic, auto-antibody positive (high risk for T1 D, but no overt disease) and recent onset (<2 years) adolescent and young adult T1 D donors. In humans SA-βgal activity in islet cells is low in adolescents and young adults but gradually increases with age. SA-βgal activity was dramatically elevated in the islets of T1D donors relative to similarly aged nondiabetic and autoantibody-positive donors. Immunostaining for CDKN1A, CDKN2A and γ-H2A.X on pancreas sections from a larger cohort of similarly aged juvenile (12-18 years old) and young adult (20-37 years old) donors from non-diabetic, autoantibody positive (autoab+) and early onset T1 D (ranging from <1 year to 6 years) was performed. CDKN2A expression was low or absent in young children donor islets (age 2), but was increased in young adult (20-25) and was highest in geriatric donors (>70 years old), consistent with age-related beta cell senescence, while CDKN1A was not detectable in any human samples throughout this age range. Strikingly, autoab+ and T1 D donors had dramatically increased expression of these senescence markers in beta cells as compared with nondiabetic donors. To determine if beta cells from T1 D donors acquired SASP, SASP markers, IL-6, SERPINE1, IL-8 and MMP9 were stained for in the same cohort. These SASP markers were clearly increased in the beta cells of autoab+ and T1 D donors relative to nondiabetic donors. On average, there was ~3-5-fold more CDKN1A$^+$ beta cells in autoab+ and recent onset T1 D donors relative to nondiabetic donors. The difference in SASP marker IL-6 was more striking, as IL-6 was expressed in ~10-14% of beta cells in the autoab+ and recent onset T1 D donors on average but was rarely observed in nondiabetic individuals.

Next, normal human donor islets were treated with the chemotherapeutic agent bleomycin to induce double-strand DNA breaks and monitored the development of stress-induced senescence and SASP by qRT-PCR and secretion assays after 5 days, coinciding with the typical onset of SASP. Notably, bleomycin treatment induced expression of CDKN1A and CDKN2A, consistent with the induction of senescence in a subset of the islet cells. Luminex assays on the CM from the bleo-treated islets showed increased levels of SASP factors IL-6, IL-8, IL-1β and TNFα compared with control islet CM. Taken together, these data indicate that beta cells harboring SASP accumulate in autoab+ and recent onset T1 D human donors and that these changes are consistent with changes occurring during the senescence of human islets in response to stress and is distinct from natural age-related beta cell senescence.

Example 3. Non-cell autonomous activities of islet SASP. To address whether the SASP of beta cells had non-cell autonomous effects resembling SASP, the ability of secreted factors from CD45-depleted islet cells of 14 wk NOD mice to induce senescence in NOD mouse embryonic fibroblasts (MEFs) and in 8 week NOD islets (when senescence is not observed) was assessed. When early passage NOD MEFs were cultured in the presence of CM from 14 wk CD45-depleted NOD islet cells (NCM) they induced Cdkn1a and Cdkn2a expression and increased SA-βgal activity, similarly to the senescent MEF CM control (SCM). The NCM was also capable of increasing the proportion of SA-βgal$^+$ cells in the cultured islets from 8 week old NOD mice.

To test whether senescence and SASP could be transmitted in a paracrine fashion to human islets, senescence was induced with bleomycin or etoposide in human BJ fibroblasts or WI-38 fibroblasts, respectively and 5 days later CM was collected. ELISA confirmed that senescent BJ cells secreted high levels of IL-6, consistent with expression of SASP. Notably, the CM from senescent BJ cells could induce paracrine senescence in WI-38 primary lung fibroblasts, and vice-versa, confirming that the senescent fibroblast CM had paracrine senescence activity. Human islets were then cultured in the presence of serum-free media (SFM) as a control or CM from the senescent fibroblasts (SCM) for 5 days and senescence and SASP markers were interrogated by qRT-PCR and secretion assays. Strikingly, islets cultured with the SCM showed increased CDKN1A and CDKN2A expression along with SASP genes IL6, IL8, and MMP3, relative to the SFM cultured islets. These islets also showed SASP secretion as evidenced by increased levels of IL-6 in the resulting islet CM.

The ability of CM from NOD islet cells and human islets to induce monocyte chemotaxis using the transwell assay was tested using the human THP-1 cell line. NCM was capable of stimulating chemotaxis 3-fold over the SFM control, similarly to the positive control, serum-free media conditioned with recombinant mouse CCL2. In addition, CM from human islets expressing SASP induced THP1 chemotaxis ~5-fold over the SFM control. Taken together, these data demonstrate that the SASP from NOD islet cells and human islets exhibits non-cell autonomous activities.

Example 4. BH3 mimetics preferentially eliminate SASP beta cells in NOD mice. To determine the role of SASP cells in the development of T1D, we next explored whether pro-survival checkpoints could be exploited to promote selective deletion of senescent beta cells. As senescent cells, like tumor cells, have been shown to upregulate members of the anti-apoptotic Bcl-2 family of proteins, immunostaining was used to assess the levels of Bcl-2 in islets of NOD mice. Bcl-2 was overexpressed in islets with SASP beta cells indicating that these cells were resistant to apoptosis and that SASP beta cells would be sensitive to drugs that interfered with the interactions of anti- and pro-apoptotic members. The Bcl-2 family contains a hydrophobic groove called the BH3 domain and 'BH3 mimetics' are pharmacological compounds that mimic the binding of the BH3-only initiator proteins to the pro-survival members. The BH3 mimetics can trigger apoptosis with some specificity in cells that have high levels of Bcl-2 or the related members. A number of small molecule inhibitors that target Bcl-2, Bcl-xL, Bcl-w or Mcl-1 proteins have been developed and some of them have been used to preferentially trigger apoptosis in senescent cells, both in vitro and in vivo. To determine which Bcl-2 pro-survival members were relevant to SASP islet cells, we treated NOD islets with BH3 mimetics that had different specificities. ABT-737 targets Bcl-2 and family members Bcl-xL and Bcl-w, ABT-199 selectively targets Bcl-2, and Maritoclax targets only Mcl-1. To determine which Bcl-2 pro-survival members were relevant to SASP islet cells, NOD islets were treated with three different BH3 mimetics that had different specificities, ABT-737, ABT-199 and Maritoclax. There was a significant reduction of both Cdkn1a and Cdkn2a mRNA from islets treated with ABT-737 or ABT-199 whereas Maritoclax did not have effects.

For studies using ABT-737, 10 week old euglycemic NOD/ShiltJ mice were given oral gavage of 100 mg/kg ABT-737 or vehicle (30% propylene glycol, 5% Tween-80 and 65% D5W) for 3 consecutive days followed by a break for 4 days and then again treated for 3 days (a total of 6 doses), and then untreated for 2 weeks followed by three consecutive days of ABT-737 or vehicle treatment and then allowed to age without further treatment until 28 weeks of age. Same outline was followed for ABT-199, wherein 11 week old euglycemic NOD/ShiltJ mice were given ABT-199 or vehicle (60% phosphal 50 PG, 30% PEG 400 and 10% ethanol) by i.p injection every alternate day for 2 weeks and then RBG was measured until 28 weeks of age. did not have any effect.

To determine whether ABT-737 targeted SASP beta cells for apoptosis in vivo, NOD mice were administered ABT-737 via oral gavage for 1 week followed by analysis of senescence and SASP markers by immunostaining. While over 50% of beta cells in islets from 12 week NOD mice expressed Cdkn2a, NOD mice administered ABT-737 showed a marked reduction in Cdkn2a. Quantification revealed that ABT-737 led to over 40% reduction in Cdkn2a$^+$ beta cells. The SASP marker Mmp2 was reduced to an even greater extent, as Mmp2$^+$ beta cells were only rarely detected in ABT-737-treated mice relative to controls.

Islets isolated from vehicle controls, ABT-737-treated mice or ABT-199-treated mice were depleted of CD45$^+$ cells and CM was collected The CM from CD45-depleted islet cells of NOD mice treated with ABT-737 or ABT-199 showed lower levels of most of the SASP factors as compared to vehicle control mice. Consistent with decreased SASP, CM from CD45-depleted islet cells of ABT-737-treated mice also showed diminished paracrine senescence activity on NOD MEFs and on 8-week NOD islet cells. Similarly, THP1 chemotaxis activity was reduced in the CM upon ABT-737 treatment of islets relative to vehicle-treated islets ex vivo.

Figure 1:
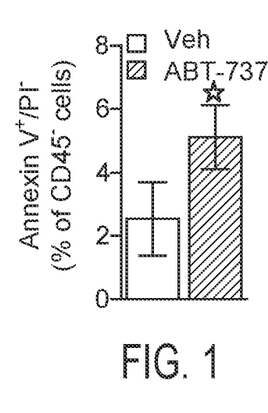
FIG. 1 depicts the abundance of apoptotic cells (Annexin $V^+$) in the CD45-(endocrine enriched) fractions of NOD islets treated with ABT-737 for two weeks, compared to control vehicle-treated mice (n=2 mice per group), error bars are s.d. *$p<0.05$, two-tailed T-test.

Example 5. Targeted depletion of SASP beta cells prevents diabetes in NOD mice The impact of senolytic treatments on immune cells was assessed. In islets from NOD mice treated with ABT-737, there was a 2-fold increase in apoptotic cells, as measured by flow cytometry for Annexin V and propidium iodide, in the endocrine compartment compared to vehicle control mice (FIG. 1). This was also confirmed by TUNEL staining to directly visualize apoptotic islets cells, in that pancreata from ABT-737 treated mice showed TUNEL$^+$ cells within the islet that were rarely observed in islets from vehicle control mice. Importantly there were no significant differences in apoptosis in the immune compartment of ABT-737-treated mice relative to vehicle controls. Flow cytometry was then used to examine the distributions and proportions of main lymphoid cell types involved in T1D in the spleen, pancreatic lymph nodes, and islets from vehicle control and ABT-737- and ABT-199-treated mice. Strikingly, this analysis revealed no significant changes in the proportions or balance of effector T cells, B cells and regulatory T cells in the treated mice relative to vehicle control mice, as well as no changes in the proportions of macrophages or dendritic cells in these tissue sites, indicating the senolytic drugs used do not target the immune compartment.

Figure 2:
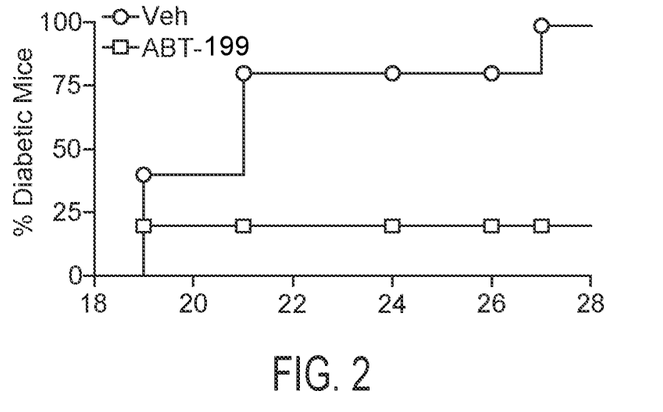
FIG. 2 depicts the incidence of diabetes in a cohort of NOD mice treated with ABT-199 (n=5) or vehicle (n=5).

To determine whether clearance of SASP beta cells prevented diabetes, 10 week euglycemic NOD mice were administered ABT-737 by oral gavage for two weeks, followed by another dose at 16 weeks and allowed to age. Strikingly, while 60% of vehicle control mice were diabetic at this time, only 40% of ABT-737-treated mice became diabetic. We performed a similar study with ABT-199, administering the drug by oral gavage for 2 weeks from 11-13 weeks of age and allowing the mice to age to 30 weeks. Remarkably, while 100% of the controls became diabetic by 28 weeks, only 10% of the ABT-199-treated mice were diabetic (FIG. 2). Taken together, these data support the conclusion that SASP beta cells promote the progression of T1 D.

Conclusions. The findings support the conclusion that pancreatic beta cells activate a cellular stress program and acquire a SASP phenotype during the development of T1 D in NOD mice and humans. In the NOD mice, beta cells with SASP were most frequently observed in islets with insulitis, consistent with the idea that immune cells trigger cellular stress in beta cells. The accumulation of SASP beta cells in T1 D suggests a failure of immune-mediated clearance. Failure to clear the SASP beta cells in a timely fashion could result in an accumulation that is likely to promote disease progression in T1 D. The clearance of SASP beta cells with senolytic agents may compensate for the failure of the immune response to SASP cell surveillance in T1 D. Targeting SASP beta cells using senolytic drugs to halt the disease and preserve functional beta cell mass provides a new paradigm for developing T1 D therapies.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of preventing Type 1 diabetes in a subject at risk therefrom,
    wherein the subject is a non-diabetic subject having one or more Type 1 diabetes risk factors;
    comprising administration of a senolytic agent to the subject; wherein the senolytic agent comprises ABT-737 or ABT-199.

2. The method of claim 1, wherein
    the or more Type 1 diabetes risk factors of the subject is selected from the group consisting of: has been diagnosed as prediabetic; has been diagnosed as having subclinical diabetes; has been diagnosed as having chemical diabetes; has Type 1 diabetes autoantibodies; and has insulitis.

* * * * *